United States Patent [19]

Kleiner et al.

[11] 4,195,035
[45] Mar. 25, 1980

[54] ALKANE-BISALKYL-PHOSPHINIC ANHYDRIDES AND PROCESS FOR THE MANUFACTURE OF ALKANE-PHOSPHONIC ANHYDRIDES AND ALKANE-BIS ALKYL-PHOSPHINIC ANHYDRIDES

[75] Inventors: Hans-Jerg Kleiner, Kronberg; Walter Dursch, Königstein, both of Fed. Rep. of Germany

[73] Assignee: Hoechst Aktiengesellschaft, Frankfurt am Main, Fed. Rep. of Germany

[21] Appl. No.: 19,786

[22] Filed: Mar. 12, 1979

[30] Foreign Application Priority Data

Mar. 17, 1978 [DE]  Fed. Rep. of Germany ....... 2811628

[51] Int. Cl.$^2$ .............................................. C07F 9/30
[52] U.S. Cl. .............................................. 260/545 P
[58] Field of Search ................................... 260/545 P

[56] References Cited

U.S. PATENT DOCUMENTS

| 3,639,473 | 2/1972 | Venezky | 260/545 P |
| 3,689,548 | 9/1972 | Maier | 260/545 P |

FOREIGN PATENT DOCUMENTS 193508   3/1967   U.S.S.R. ............... 260/545 P

OTHER PUBLICATIONS

Michaelis et al., "Ber", Jahreg VII, p. 1070 (1874).
Kosolapoff et al., "JACS", 73:4101 (1951).
Moedritzer, "JACS", 83:4381 (1961).

*Primary Examiner*—Norman Morgenstern
*Attorney, Agent, or Firm*—Connolly and Hutz

[57] ABSTRACT

Alkane-bisalkylphosphinic anhydrides consisting of repeating units of the formula

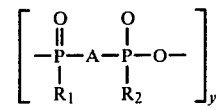

and process for the manufacture of alkane-phosphonicanhydrides and alkane-bisalkyl-phosphonic anhydrides consisting of repeating units of the formula

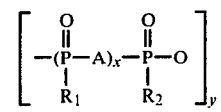

wherein alkane-phosphonic acids or alkane-bisalkyl-phosphinic acids of the formula

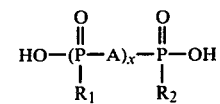

are heated to 250° to 450° C. under reduced pressure while splitting off water.

3 Claims, No Drawings

ALKANE-BISALKYL-PHOSPHINIC ANHYDRIDES AND PROCESS FOR THE MANUFACTURE OF ALKANE-PHOSPHONIC ANHYDRIDES AND ALKANE-BIS ALKYL-PHOSPHINIC ANHYDRIDES

Various processes are known for the manufacture of alkane-phosphonic anhydrides, of which those using phosphonic acids as starting materials are of special interest. It is known first to transform the phosphonic acids into the phosphonic acid dichloride with the use of phosphorus pentachloride and to prepare the anhydride by heating the phosphonic acid dichloride together with phosphonic acid.

The present invention is based on the observation that phosphonic acids as well as alkane-bisalkyl-phosphinic acids can be transformed into the corresponding anhydrides by thermal dehydration without auxiliary agent.

It is the object of the present invention to provide alkane-bisalkyl-phosphinic anhydrides of the formula I

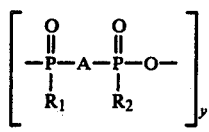

in which $R_1$ and $R_2$ denote alkyl having from 1 to 20, preferably from 1 to 8 and more preferably from 1 to 4, carbon atoms, A is alkylene having from 1 to 20, preferably from 1 to 8 and more preferably from 1 to 4, carbon atoms and y is an integer equal to or greater than 1.

It is further object of the present invention to provide a process for the manufacture of alkane-phosphonic anhydrides and alkane-bisalkyl-phosphinic anhydrides of the formula II

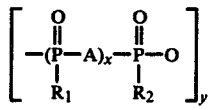

in which $R_1$ and $R_2$ denote alkyl having from 1 to 20, preferably from 1 to 8 and more preferably from 1 to 4, carbon atoms, A is alkylene having from 1 to 20, preferably from 1 to 8 and more preferably from 1 to 4, carbon atoms, x is zero or 1 and y is an integer equal to or greater than 1, which comprises heating to 250° to 450° C. alkane-phosphonic acids or alkane-bisalkyl-phosphinic acids of the formula III

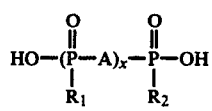

in which $R_1$, $R_2$ and x have the aforesaid meaning, under reduced pressure and with splitting off of water.

Suitable starting compounds for the process of the invention are, for example, the following acids: methane-phosphonic acid, ethane-phosphonic acid, propane-phosphonic acid, butane-phosphonic acid, hexane-phosphonic acid, octane-phosphonic acid, decane-phosphonic acid, eicosane-phosphonic acid, methane-pyrophosphonic acid, propane-pyrophosphonic acid, methane-bis(methylphosphinic acid), methane-bis(ethylphosphinic acid), methane-bis(propylphosphinic acid), ethane-1,2-bis(methylphosphinic acid), propane-1,3-bis(methylphosphinic acid), butane-1,4-bis(methylphosphinic acid), hexane-1,6-bis(methylphosphinic acid) and decane-(1,10-bismethylphosphinic acid).

The acids are heated to a temperature of from 250° to 450° C., preferably 280° to 360° C. under reduced pressure in the range of from 0.01 to 100 torr, preferably 0.1 to 25 torr and more preferably 1 to 5 torr. The lower the pressure the lower the reaction temperature. The water split off can be condensed, for example in a cooling trap following the reaction vessel. The process can also be carried out continuously, for example by passing the starting product through a tube heated by electric means.

Still further, it has been found that the compounds of formula II in which X is zero and $R_2$ is $C_1$-$C_8$alkyl and compounds in which X is 1 and A stands for $C_1$-$C_8$alkylene, especially $C_1$-$C_4$alkylene, and $R_1$ and $R_2$ are $C_1$-$C_4$alkyl can be distilled under the aforesaid reaction conditions. They distill out of the reaction vessel in the measure they are formed and are purified in this manner.

In general, the anhydrides are obtained in the form of linear polymers the degree of polymerization of which, designated by y in the formulae I and II, is not known. The terminal groups of the polymer chain are formed by hydrogen or hydroxy. In individual cases, cyclic compounds are obtained. It can be assumed that such cyclic compounds are also present during the distillation described above.

The manufacturing conditions can be chosen in such a manner that the alkane-phosphonic anhydrides and alkane-bis-phosphinic anhydrides obtained are completely free from the starting acids. With processes on an industrial scale, which should be as rapid as possible, small amounts of the starting compounds may remain in the final products. In general, the content of residual acid will not exceed 10% by weight. Reaction products of this type are suitable without restriction for numerous further reactions. It is also possible, of course, to adjust in the final products any desired content of residual acid. If, for example, an anhydride with a content of residual acid of 30% is wanted, the splitting off of water in continued to a degree of 70%.

The process of the invention is surprising in that it has been known that with phenyl phosphonic acid the starting compound is decomposed into benzene and meta-phosphorus acid at temperatures above 250° C. (cf. A. Michaelis et al., Chem. Ber. 7, 1070 (1874)). Consequently, the formation of olefins or ethers as decomposition products of a pyrolysis could have been expected. It is especially surprising that the reaction products are capable of being distilled under the reaction conditions.

The alkane-phosphonic anhydrides and alkane bisalkyl-phosphinic anhydrides according to the invention are valuable intermediates. They can be used, for example, for the manufacture of flame retardants as described in U.S. Pat. Appl. Ser. No. 913,083, for metal extraction, as anti-corrosive agents, or for the manufacture of antistatic agents.

The following examples illustrate the invention.

EXAMPLE 1

In a glass flask with mounted, non metallized, 12 cm Vigreux column and connected air condenser with receiver 220 g of ethane-phosphonic acid are heated to an internal temperature of 300° to 320° C. for 12 hours under a pressure of 0.2 to 0.5 torr.

The ethane-phosphonic anhydride formed distills over at a transition temperature of 195° to 200° C. In a cooling trap following the apparatus 36 g of water are collected.

175 g of ethane-phosphonic anhydride are obtained, corresponding to a yield of 95% of the theory.

EXAMPLE 2

In the apparatus described in Example 1, 211 g of propane-phosphonic acid are heated to an internal temperature of 360° to 420° C. for 2.5 hours under a pressure of 25 torr.

At a transition temperature of 320° C. propane-phosphonic anhydride distills over. 170 g are obtained, corresponding to a yield of 95% of the theory.

EXAMPLE 3

In the apparatus described in Example 1, 138 g of butane-phosphonic acid are heated to an internal temperature of 220° C., which is raised to 280° C. during the course of 4 hours, and under 1 torr. Water collects in the cooling trap following the apparatus. At an internal temperature of 300° to 320° C. butane-phosphonic anhydride is then distilled off for 7 hours at 0.4 torr and a transition temperature of 185° to 200° C.

110 g of butane-phosphonic anhydride are obtained in the form of a viscous oil, corresponding to a yield of 92% of the theory.

EXAMPLE 4

In the apparatus described in Example 1, 200 g of hexane-phosphonic acid are heated to a temperature of at most 340° C. and under 0.3 torr. At a transition temperature of 225° to 250° C. hexane-phosphonic anhydride distills off over a period of 10 hours. In a cooling trap following the apparatus about 22 g of water condense.

170 g of hexane-phosphonic anhydride, $n_D^{24} = 1.4670$, are obtained, corresponding to a yield of 95% of the theory.

EXAMPLE 5

In the apparatus described in Example 1, 194 g of octane-phosphonic acid are heated to an internal temperature of 300° to 360° C. and under about 1 torr. After 5 hours the internal temperature is raised to 370° to 410° C. After a further 3 hours 172 g of crude octane-phosphonic anhydride are obtained which is subsequently distilled.

The pure octane-phosphonic anhydride obtained has a boiling point of 300° to 350° C. under 0.8 torr. The yield of crude reaction product amounts to 100% of the theory.

EXAMPLE 6

In the apparatus described in Example 1, 93 g of ethane-1,2-bis(methylphosphinic acid) are heated to 300° to 320° C. under a pressure of 1 torr. In a cooling trap following the apparatus water is collected and simultaneously ethane-1,2-bis(methylphosphinic anhydride) distills off. 87 g of anhydride having a boiling point of 230° C. under 1 torr and a solidification point of 115° to 120° C. are obtained in the form of a glass-like mass, corresponding to a yield of 93% of the theory.

EXAMPLE 7

In the apparatus described in Example 1, 50 g of propane-1,3-bis(methylphosphinic acid) are heated to 250° C. under a pressure of 0.5 torr. The temperature is gradually raised to 280° C. At a transition temperature of about 200° C. propane-1,3-bis(methylphosphinic)-anhydride distills off, which is subjected to another distillation.

40 g of propane-1,3-bis(methylphosphinic)-anhydride are obtained, b.p. 163° C. under 0.3 torr, s.p. 122° to 130° C., corresponding to a yield of 86% of the theory.

According to the $^1$H-NMR spectrum the product has the structural formula

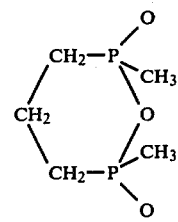

$\delta CH_3$ [doublet; $J_{CH_3,P} = 14$ Hz]: 1.75 ppm$^{(+)}$
$\delta(CH_2)_3$ [multiplet]: 1.5–2.5 ppm$^{(+)}$
$^{(+)}$ in CDCl$_3$

EXAMPLE 8

In the apparatus described in Example 1, 80 g of butane-1,4-bis(methylphosphinic acid) are heated to an internal temperature of 290° to 320° C. and under a pressure of 0.5 torr. At a transition temperature of about 200° C. the butane-1,4-bis(methylphosphinic)-anhydride distills off. It is subjected to another distillation.

65 g of butane-1,4-bis(methylphosphinic)-anhydride having a boiling point of 185° C. under 0.5 torr and a solidification point of 65° C. are obtained in the form of a glass-like mass, corresponding to a yield of 88% of the theory.

What is claimed is:

1. A process for the manufacture of alkane-phosphonic anhydrides and alkane-bisalkyl-phosphinic anhydrides of the formula II

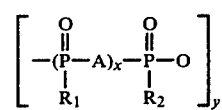

in which $R_1$ and $R_2$ are alkyl having from 1 to 20 carbon atoms, A is alkylene having from 1 to 20 carbon atoms, x is zero or 1 and y is an integer equal to or greater than 1, which comprises heating to 250° to 450° C. an alkane-phosphonic acid or alkane-bisalkyl-phosphinic acid of the formula III

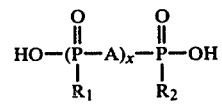

in which $R_1$, $R_2$ and x have the aforesaid meaning, under reduced pressure and with splitting off of water.

2. A process as claimed in claim 1 for the manufacture of a compound of formula II wherein $R_1$ and $R_2$ are alkyl with 1 to 8 carbon atoms and A is alkylene with 1 to 8 carbon atoms.

3. A process as claimed in claim 1 for the manufacture of a compound of formula II wherein $R_1$ and $R_2$ are alkyl with 1 to 4 carbon atoms and A is alkylene with 1 to 4 carbon atoms.

* * * * *